United States Patent
Seo et al.

(10) Patent No.: US 10,413,245 B2
(45) Date of Patent: Sep. 17, 2019

(54) DETECTION APPARATUS OF VITAL PARAMETERS ON STEERING WHEEL

(71) Applicants: Hyundai Motor Company, Seoul (KR); Daesung Electric Co., Ltd., Ansan, Gyeonggi-do (KR)

(72) Inventors: Hai Jin Seo, Gyeonggi-do (KR); Shin Hae Kim, Gyeonggi-do (KR); Jong Il Yu, Gyeonggi-do (KR); Won Ho Shin, Seoul (KR); Sung Hwan Shin, Gyeonggi-do (KR); Chan Gug Park, Gyeonggi-do (KR)

(73) Assignees: Hyundai Motor Company, Seoul (KR); LS Automotive Technologies Co., Ltd., Anyang, Gyeonggi-Do (KR)

( * ) Notice: Subject to any disclaimer, the term of this patent is extended or adjusted under 35 U.S.C. 154(b) by 279 days.

(21) Appl. No.: 15/265,950

(22) Filed: Sep. 15, 2016

(65) Prior Publication Data

US 2017/0273630 A1 Sep. 28, 2017

(30) Foreign Application Priority Data

Mar. 25, 2016 (KR) .................... 10-2016-0036347

(51) Int. Cl.

| | |
|---|---|
| *A61B 5/00* | (2006.01) |
| *A61B 5/0205* | (2006.01) |
| *B62D 1/04* | (2006.01) |
| *B60K 28/02* | (2006.01) |
| *A61B 5/024* | (2006.01) |

(Continued)

(52) U.S. Cl.
CPC .......... *A61B 5/6893* (2013.01); *A61B 5/0205* (2013.01); *B60K 28/02* (2013.01); *B62D 1/046* (2013.01); *A61B 5/02416* (2013.01); *A61B 5/0533* (2013.01); *A61B 5/14551* (2013.01); *A61B 5/4872* (2013.01); *A61B 2562/0238* (2013.01); *A61B 2562/166* (2013.01); *A61B 2562/185* (2013.01); *B60Y 2302/03* (2013.01)

(58) Field of Classification Search
CPC .............................. A61B 5/18; A61B 5/6893
See application file for complete search history.

(56) References Cited

U.S. PATENT DOCUMENTS

| | | | |
|---|---|---|---|
| 2008/0238695 A1 | 10/2008 | Yanai et al. | |
| 2014/0135598 A1* | 5/2014 | Weidl | A61B 5/0205 |
| | | | 600/301 |
| 2014/0316227 A1 | 10/2014 | Rake et al. | |

FOREIGN PATENT DOCUMENTS

| | | | | |
|---|---|---|---|---|
| CN | 103957796 B | * | 12/2015 | ............ B62D 1/046 |
| JP | 2008-237378 A | | 10/2008 | |

(Continued)

*Primary Examiner* — Michael J D Abreu
(74) *Attorney, Agent, or Firm* — Mintz Levin Cohn Ferris Glovsky and Popeo, P.C.; Peter F. Corless (57) ABSTRACT

A detection apparatus of vital parameters on a steering wheel is provided. The apparatus includes a horn switch, remote control switches configured to operate devices within a vehicle and a vital signal detector configured to detect a vital signal of an operator. The vital signal detector includes a detection sensor that is configured to detect the vital signal of the operator and a photo sensor that is mounted on the remote control switch. Accordingly, the separate space for the assembling portion of the vital signal detector is not required and the volume of the apparatus and the number of components are reduced. The mountability and the aesthetics are improved.

12 Claims, 10 Drawing Sheets

(51) Int. Cl.
*A61B 5/053* (2006.01)
*A61B 5/1455* (2006.01)

(56) References Cited

FOREIGN PATENT DOCUMENTS

JP          4962360 B2    6/2012
JP          5375747 B2   12/2013
KR     2014-0096290 A    8/2014

\* cited by examiner

DETECTION APPARATUS OF VITAL PARAMETERS ON STEERING WHEEL

CROSS-REFERENCE TO RELATED APPLICATION

This application is based on and claims the benefit of priority to Korean Patent Application No. 10-2016-0036347, filed on Mar. 25, 2016 in the Korean Intellectual Property Office, the disclosure of which is incorporated herein in its entirety by reference.

BACKGROUND

(a) Field of the Invention

The present invention relates to a detection apparatus of vital parameters on a steering wheel, and more particularly, to a detection apparatus in which the vital parameters are included in a remote control switch.

(b) Description of the Related Art

Recently, a vehicle has become a space which may receive a variety of information and services associated with traffic, economy, culture, and daily life during operation of the vehicle due to the development of the Internet and an IT technology. Accordingly, the safety and convenience of a driver are significantly improved and the vehicle is used as information and business and a leisure space beyond a simple method of transportation.

Further, a technology on safety of a driver and ubiquitous-healthcare (u-Healthcare) are applied to a vehicle. The u-Healthcare is installed within a vehicle to increase safety and convenience of a driver and maintain a concept of health care even during operation of the vehicle. For example, a u-Healthcare system includes a combination of IT with health and medical care that may be used anytime, anywhere and serves remote management of diseases and health maintenance. In particular, a vehicle driver receives a vital signal in a nonrestrictive state during operation of the vehicle and analyzes the health information and transmits the analyzed health information to the driver or transmits the analyzed health information to a driver's health care system.

A vital signal detecting system using optical plethysmography (e.g., volume change measurement) and pulse oximetry (e.g., oxygen saturation measurement) to detect human vital parameters. Generally, a non-invasive examination of a pulse rate, variability of the pulse rate, and arterial oxygen saturation is performed by referring to a light absorption measurement value or a light reflection measurement value when light is transmitted through a tissue. The similar measurement methods are based on the plethysmography and the pulse oximetry. The plethysmography is performed by referring to an optical measurement value for a change in light absorption appearing by a volume change of a blood vessel. Further, the pulse oximetry is based on different light absorption or light reflectance of red measurement rays and infrared measurement rays (e.g., relies on blood oxygen saturation) when radiation transmits a skin and a tissue.

The pulse oximetry generally uses a photo sensor to examine an oxygen saturation value (e.g., SPO2-value) of a finger, a toe, or an earlobe. In particular, the measurement is performed by a clip type sensor or a patch type sensor. In other words, the sensors are typically a photo sensor and a photodiode and include one or two light sources in, for example, a red diode and/or an infrared diode type. The infrared diode emits light in an invisible area of electromagnetic spectrum and the red diode radiates light in a visible area. Further, blood-hemoglobin more or less saturated with oxygen is colored differently. Therefore, different absorption coefficients recorded by the photo sensor are generated for the red light or the infrared light to be irradiated. Generally, a photoelectron sensor may also determine a pulse, a pulse wave, a pulse rate, and variability of the pulse rate, in addition to the oxygen saturation. To address the limited freedom of movement while a vehicle drives, attempts to integrate the foregoing photo sensors in operation elements of a vehicle have been developed. An object of the attempts is to detect vital parameters while minimizing an influence on a driver.

The measurement methods integrate photo sensors in a steering wheel rim of a vehicle. However, when the photo sensors are disposed in the steering wheel rim, brightness may be variable when the photo sensors approach a windshield of a vehicle due to a narrow space condition is the finger posture of a driver that is required to obtain a measurement is difficult to reproduce. Accordingly, an insufficient quality of signal for optical measurement may frequently occur.

The above information disclosed in this section is merely for enhancement of understanding of the background of the invention and therefore it may contain information that does not form the prior art that is already known in this country to a person of ordinary skill in the art.

SUMMARY

The present disclosure provides a detection apparatus of vital parameters on a steering wheel capable of more stably detecting the vital parameters by integrating a conductive sensor and photo sensors in a remote control switch of the steering wheel. The detection apparatus of vital parameters improves the spatiality and facilitates an operation by reducing a volume and the number of components of the apparatus. However, problems of the present disclosure are not limited to the above-mentioned matters and other problems which are not mentioned may be clearly understood to those skilled in the art from the following descriptions.

According to an exemplary embodiment of the present disclosure, a detection apparatus of vital parameters on a steering wheel may include a horn switch, remote control switches configured to operate devices within a vehicle and a vital signal detector configured to detect a vital signal of an operator. The vital signal detector may include a detection sensor configured to detect the vital signal of the operator and a photo sensor may be mounted on the remote control switch. In the vital signal detector, a portion of the detection sensor and the photo sensor may be exposed outside the remote control switch. The vital signal detector may be disposed to abut the steering wheel (e.g., to be within a touch range by a part of an operator's body when the operator grips the steering wheel). The detection sensor and the photo sensor may have a concave shape based on a predetermined curvature (e.g., based on a curve of a body part). The photo sensor may further include an optical lens and limit a contact area to a predetermined length and width to reduce an influence by external light that transmits through the optical lens. The detection sensor may include a plurality of conductors and the optical lens may be disposed between the plurality of conductors.

The vital signal detector may include a printed circuit board that has a light receiving element configured to absorb light and a light emitting element configured to emit light.

The optical lens may maintain a distance between the light receiving element and the light emitting element and may be coupled with the printed circuit board. The vital signal detector may be configured to detect at least one of galvanic skin reflex, bioelectrical impedance analysis, photoplethysmography, or body mass index by a touch of a operator.

The remote control switches may be disposed in the horn switch to face each other and each may be provided with the vital signal detector. The printed circuit board may be formed with bolting bore that a bolt fixing the conductor and the optical lens may be configured to penetrate. The printed circuit board may be formed with apertures proximate to the bolting apertures and the detection sensor may be formed with a solder portion inserted into the aperture.

The optical lens may be disposed between the printed circuit board and the detection sensor to be fixed to the printed circuit board by the coupling with the detection sensor. A plurality of apertures may be formed in plural and may include a bead that connects between the apertures. The bead may pass through the bolting bore and may be formed with a bead aperture through which the bolt penetrate.

BRIEF DESCRIPTION OF THE DRAWINGS

The above and other objects, features and advantages of the present disclosure will be more clearly understood from the following detailed description when taken in conjunction with the accompanying drawings in which.

DETAILED DESCRIPTION

Various advantages and features of the present disclosure and methods accomplishing thereof will become apparent from the following description of exemplary embodiments with reference to the accompanying drawings. However, the present disclosure is not be limited to the embodiments set forth herein but may be implemented in many different forms. The present exemplary embodiments may be provided so that the disclosure of the present disclosure will be complete, and will fully convey the scope of the disclosure to those skilled in the art and therefore the present disclosure will be defined within the scope of claims. Like reference numerals throughout the description denote like elements.

While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other exemplary embodiments, which may be included within the spirit and scope of the invention as defined by the appended claims.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. For example, in order to make the description of the present invention clear, unrelated parts are not shown and, the thicknesses of layers and regions are exaggerated for clarity. Further, when it is stated that a layer is "on" another layer or substrate, the layer may be directly on another layer or substrate or a third layer may be disposed there between.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicle in general such as passenger automobiles including sports utility vehicles (SUV), buses, trucks, various commercial vehicles, watercraft including a variety of boats, ships, aircraft, and the like and includes hybrid vehicles, electric vehicles, combustion, plug-in hybrid electric vehicles, hydrogen-powered vehicles and other alternative fuel vehicles (e.g. fuels derived from resources other than petroleum).

Figure 1:
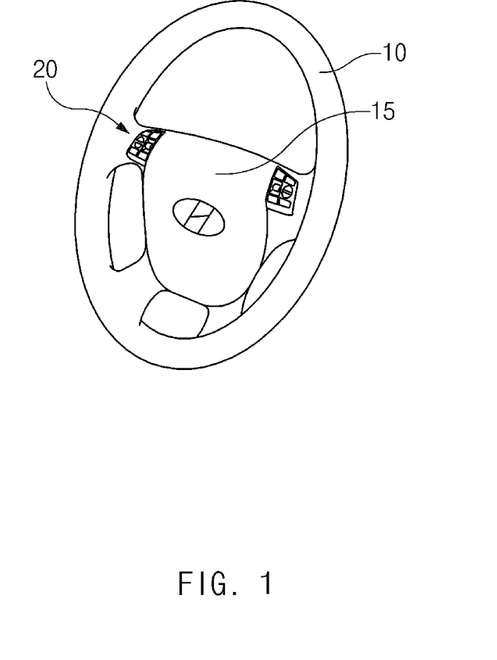
FIG. 1 is an exemplary perspective view illustrating a detection apparatus of vital parameters on a steering wheel according to an exemplary embodiment of the present disclosure.
Figure 2:
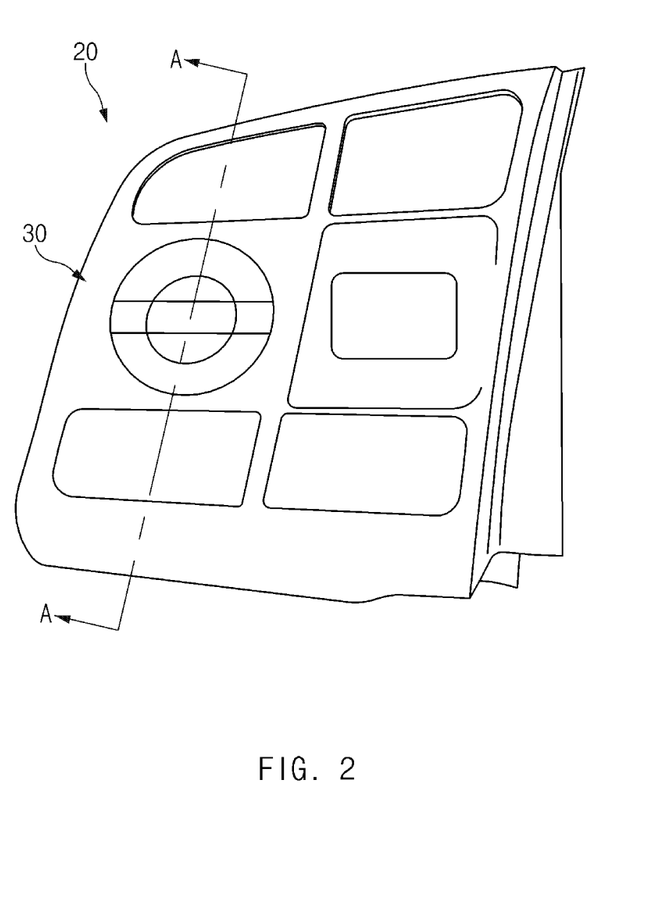
FIG. 2 is an exemplary enlarged plan view of a part of FIG. 1 according to an exemplary embodiment of the present disclosure.
Figure 3:
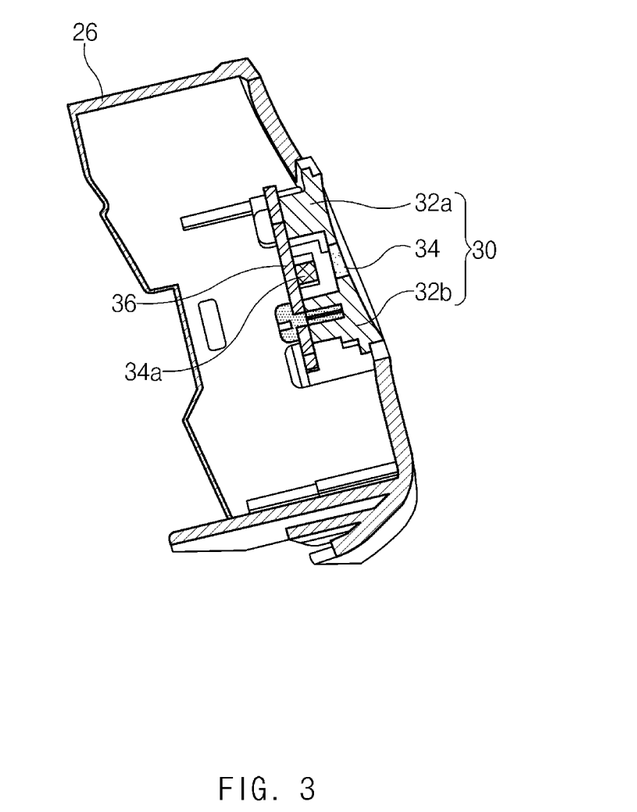
FIG. 3 is an exemplary cross-sectional view taken along A-A of FIG. 2 according to an exemplary embodiment of the present disclosure.
Figure 4:
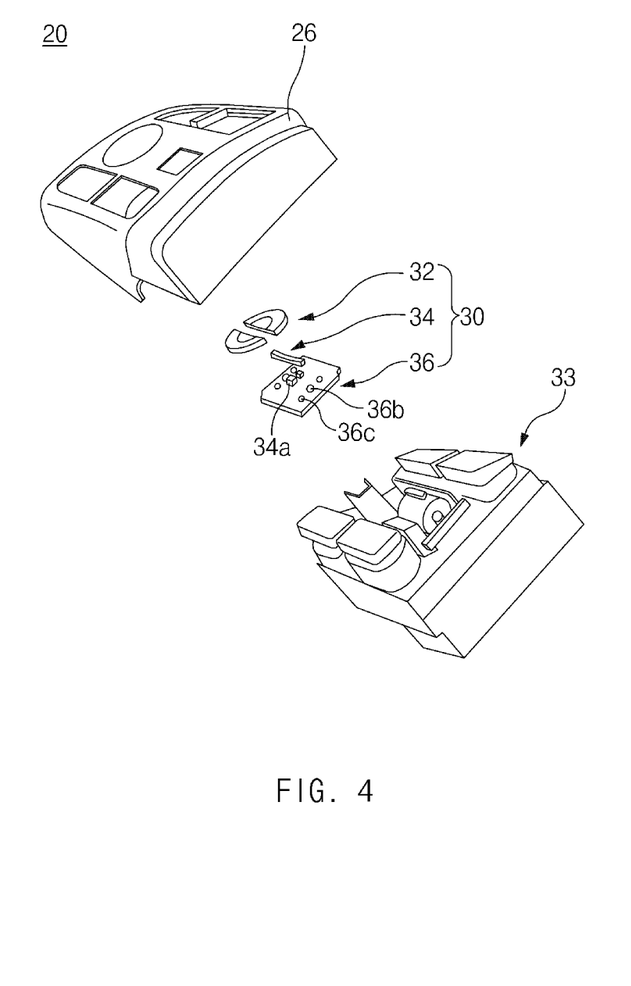
FIG. 4 is an exemplary exploded perspective view of FIG. 2 according to an exemplary embodiment of the present disclosure.
Figure 5:
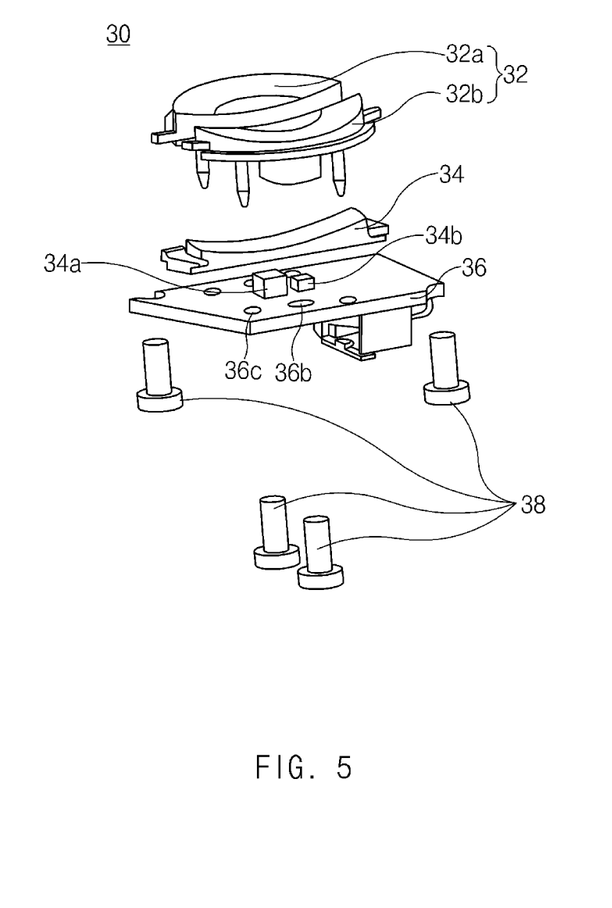
FIGS. 5 and 6 are exemplary exploded perspective views of a vital signal detector of FIG. 4 according to an exemplary embodiment of the present disclosure.
Figure 6:
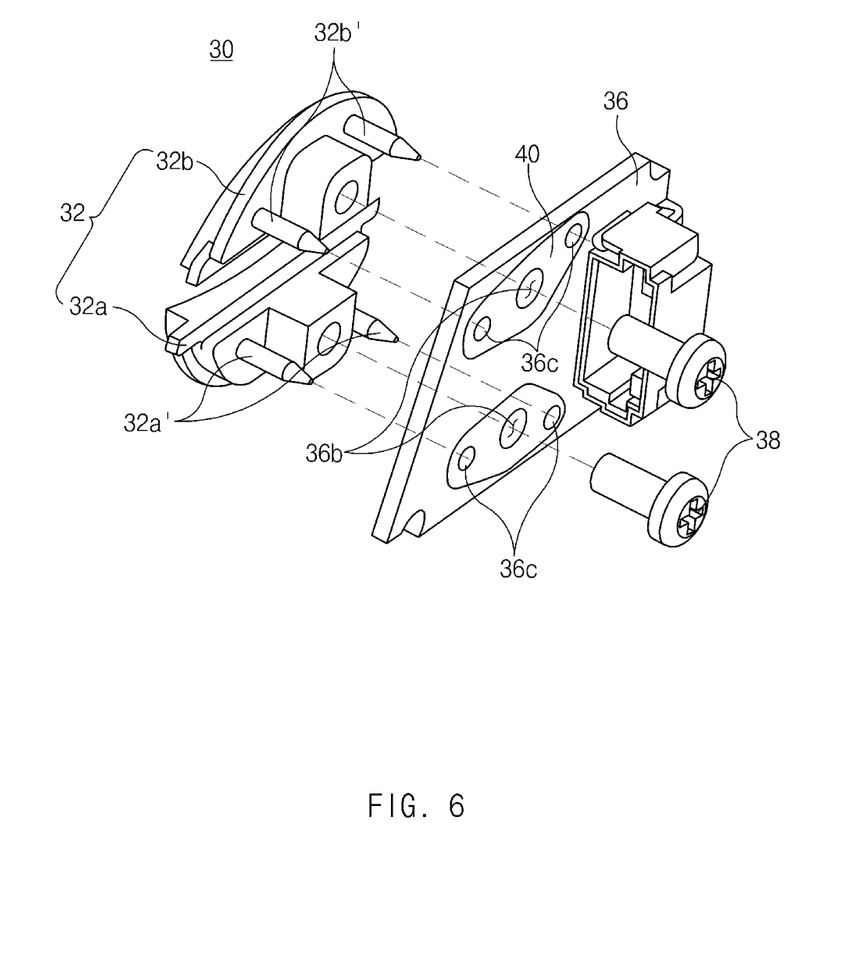
Figure 7A:
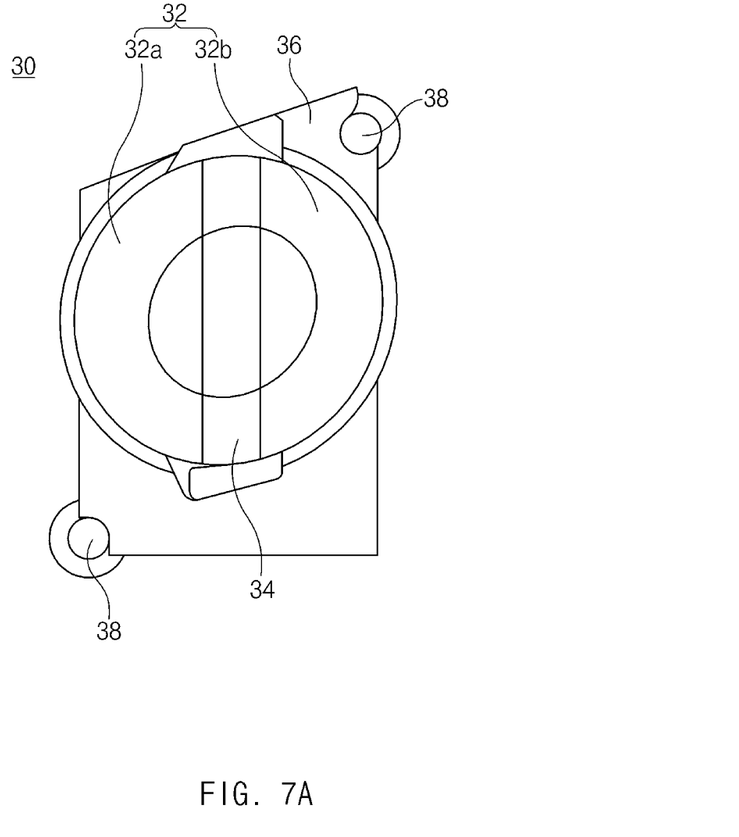
FIG. 7A is an exemplary plan view of the vital signal detector according to an exemplary embodiment of the present disclosure.
Figure 7B:
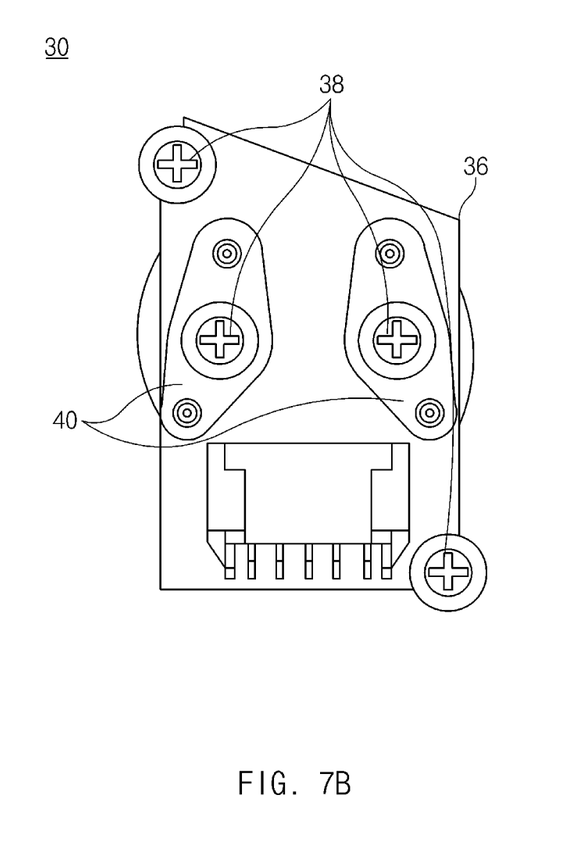
FIG. 7B is an exemplary bottom view of the vital signal detector according to an exemplary embodiment of the present disclosure.
Figure 8A:
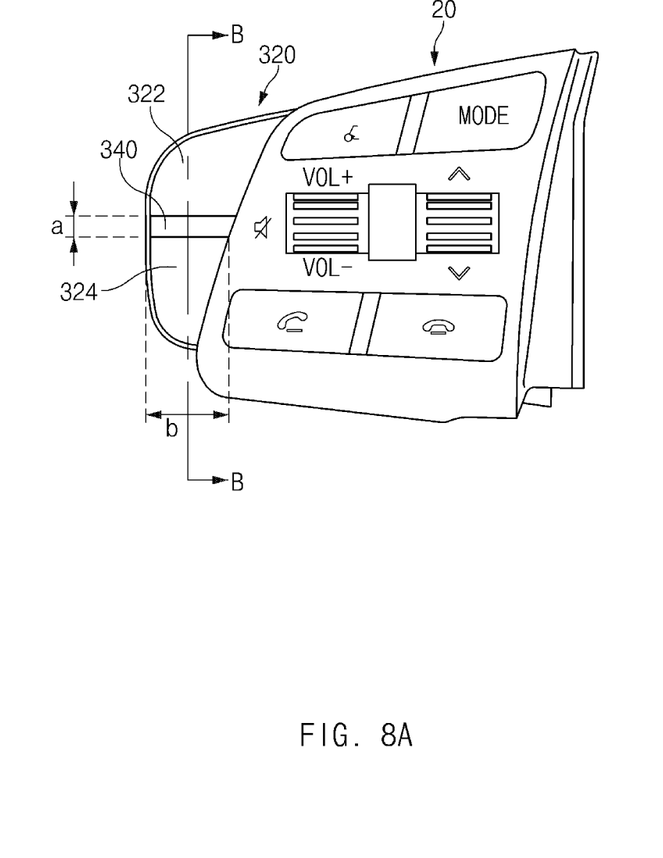
FIGS. 8A and 8B are exemplary diagrams illustrating another exemplary embodiment of the present disclosure.
Figure 8B:
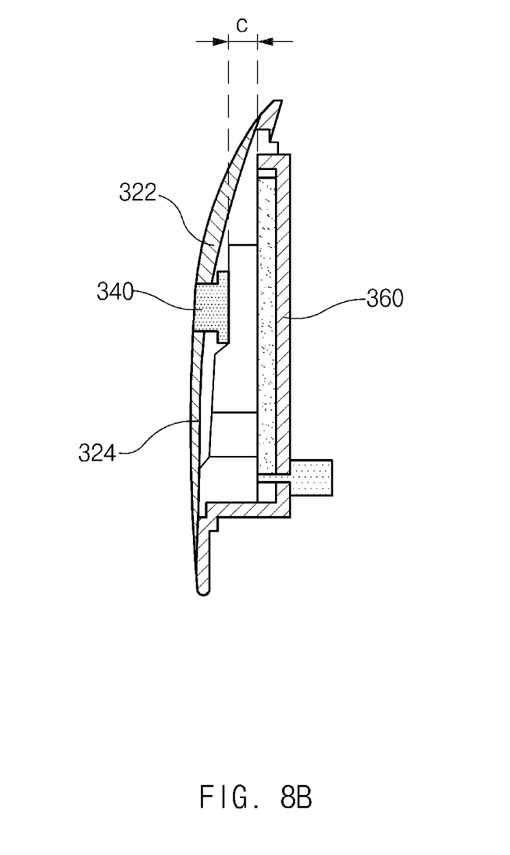

Hereinafter, a detection apparatus of vital parameters on a steering wheel according to exemplary embodiments of the present disclosure will be described with reference to the accompanying drawings FIG. 1 is an exemplary perspective view illustrating a detection apparatus of vital parameters on a steering wheel according to an exemplary embodiment of the present disclosure. FIG. 2 is an exemplary enlarged plan view of a part of FIG. 1. FIG. 3 is an exemplary cross-sectional view taken along A-A of FIG. 2. FIG. 4 is an exemplary exploded perspective view of FIG. 2. FIGS. 5 and 6 are exemplary exploded perspective views of a vital signal detector of FIG. 4. FIG. 7A is an exemplary plan view of the vital signal detector. FIG. 7B is an exemplary bottom view of the vital signal detector. FIGS. 8A and 8B are exemplary diagrams illustrating another exemplary embodiment of the present disclosure. A preferable detection apparatus of vital parameters on a steering wheel of a vehicle may be adjusted by a person having ordinary skill in the art to which the present disclosure pertains and the present embodiment corresponds to the detection apparatus of vital parameters on a steering wheel.

Referring to FIGS. 1 to 4, the detection apparatus of vital parameters on the steering wheel according to the exemplary embodiment of the present disclosure may include a steering wheel 10, a remote control switch 20 mounted on the steering wheel 10 and operating devices within a vehicle and a vital signal detector 30 disposed on the remote control switch 20 to abut the steering wheel 10 and configured to detect a vital signal of an operator. The steering wheel 10 may include a horn switch 15 disposed at a center of a rim which may be gripped by the operator (e.g., driver). The remote control switch 20 may be mounted in the horn switch 15. Additionally, a plurality of remote control switch 20 may be provided in plural and the remote control switches 20 may be disposed in the horn switch 15 to face each other.

The remote control switch 20 may be mounted on the steering wheel 10 to operate the devices within the vehicle. The remote control switch 20 may include switch type operation members and may be configured to adjust apparatuses such as a trim computer, a cruise, a hands-free, and an audio of the vehicle in a button form. The remote control switch 20 may include integrated buttons. Therefore, an operator (e.g., driver) may operate the buttons without resistance upon the operation of the buttons when gripping the steering wheel 10. The remote control switch 20 may include a button portion configured to operate the devices within the vehicle. The remote control switch 20 may have a base 23 that accommodates the vital signal detector 30. The remote control switch 20 may include a cover 26 with a plurality of button apertures formed thereon.

The cover 26 may be coupled with the base 23 to cover the base 23 at an upper portion of the vital signal detector 30. The cover 26 may be formed with the plurality of button apertures. A portion of the vital signal detector 30 may be exposed outside the remote control switch 20 and therefore may be contacted by an operator. A conductive portion of the vital signal detector 30 may be formed on a surface of the remote control switch and may be smoothly gripped by a driver to detect vital parameters that may include galvanic skin reflex, bioelectrical impedance analysis, photoplethysmography, and body mass index or the like. The vital signal detector 30 may be configured to detect at least one of the galvanic skin reflex, the bioelectrical impedance analysis, the photoplethysmography, and the body mass index by a touch of an operator that may be used for standard monitoring and diagnosis of the operator.

The detection apparatus of vital parameters on a steering wheel according to the exemplary embodiment of the present disclosure with reference to FIGS. 5 to 7B, the vital signal detector 30 may be disposed in the remote control switch 20 mounted on the steering wheel 10 to abut the rim of the steering wheel 10. In particular, the vital signal detector 30 may be disposed to be positioned within a touch range of a finger when an operator (e.g., driver) grips the steering wheel 10. The vital signal detector 30 may be disposed between the plurality of button apertures and may have a depressed concave shape to contact a tip of a finger, and may be configured to detect optical vital parameters.

The vital signal detector 30 may include a detection sensor 32 and photo sensors 34, 34a, and 34b. A portion of the vital signal detector 30 may be exposed outside the remote control switch 20. The vital signal detector 30 may be exposed to the environment on the exterior of the remote control sensor via any one of the plurality of button apertures. The vital signal detector 30 may contact a portion of an operator's body. The vital signal detector 30 may be disposed at the left and the right of the remote control switch 20 to contact a portion of a body gripping the rim. The vital signal detector 30 may include a detection sensor 32 configured to detect a vital signal of an operator and a printed circuit board 36 have photo sensors 34, 34a, and 34b.

The printed circuit board 36 may be coupled with the detection sensor 32 and the photo sensors 34, 34a, and 34b. The printed circuit board 36 may be formed with bolting bore 36b through which bolts 38 may penetrate to fix the position of detection sensor 32 and the photo sensors 34, 34a, 34b and may be formed with a plurality of bores 36c. The apertures 36c may be proximate to the bolting bores 36b. The printed circuit board 36 may be formed with the bolting bores 36b through which the bolts 38 penetrate. A first side of the printed circuit board 36 may be formed with the detection sensor 32 and the photo sensors 34, 34a, and 34b. A second side of the printed circuit board 36 may be fastened with the detection sensor 32 when the bolt 38 penetrate through the bolting bore 36b. Therefore, the detection sensor 32 and the printed circuit board 36 may be fixed by the bolt 38.

The printed circuit board 36 may include a bead 40 that connects between the apertures 36c to increase a contact surface of the bolt 38. The bead 40 may be disposed between the plurality of apertures 36c to connect between the apertures 36c, to increase a contact surface of solder portions 32a' and 32b'. The bead 40 may be disposed to pass through the bolting hole 36b. The bead 40 may be formed with a bead aperture through which the bolt 38 penetrate and a centrifugation of the bead aperture may be disposed to coincide with that of the bolting bore 36b.

Further, a current value measured by the vital signal detector 30 may be measured based on a micro value. However, when a driver operates the remote control switch 20, a current may not stably flow due to a strong force or a vehicle vibration. When the detection sensor 32 and the printed circuit board 36 are disconnected from each other the vital parameters may not be detected. However, when the printed circuit board 36 and the detection sensor 32 are fixed by the bolt 38 and the detection sensor 32 is fixed to both sides of the printed circuit board 36 by the soldering of the solder portions 32a' and 32b', the fixed force of the detection sensor 32 may be improved. Accordingly, the current flows more stably despite the vehicle vibration and the force of the driver, and may be configured to detect the vital signal.

The detection sensor 32 may include a plurality of conductors 32a and 32b to measure a micro current value. The detection sensor 32 may be formed of materials (e.g., silver, aluminum, copper, or the like) having excellent conductivity to transfer a current from an operator's (e.g., driver's) hand. The detection sensor 32 may be protrudedly formed with the solder portions 32a' and 32b' and may be inserted into the bolting bores 36b. The solder portions 32a' and 32b' may be formed in the plurality of conductors 32a and 32b, respectively. The solder portions 32a' and 32b' may be inserted into the bolting bores 36b and may then be soldered. Therefore, the detection sensor 32 may be prevented from being separated even by the vehicle vibration and the force of the driver due to the fastening of the bolt 38 and the soldering of the solder portions 32a' and 32b' and may maintain a more stable flow of current.

The photo sensors 34, 34a, and 34b may be disposed between the plurality of conductors 32a and 32b. Therefore, the flow of current may be more stably maintained despite the vehicle vibration and the force of the driver due to the solder. The photo sensors 34, 34a, and 34b may be coupled with the detection sensor 32 to insert the solder portions 32a' and 32b' into the printed circuit board 36 and then solder them. The photo sensors 34, 34a, and 34b may be formed from photoplethysmography (PPG). The photo sensors 34, 34a, and 34b may include a light receiving element 34a configured to absorb light, a light emitting element 34b configured to emit light, and an optical lens 34 disposed on the printed circuit board 36. The photo sensors 34, 34a, and 34b may limit the contact area to a predetermined length and width to reduce the influence by external light that may be transmitted the optical lens 34. Additionally, the detection sensor 32 and the optical lens 34 may be coupled with the printed circuit board 36 to consistently maintain a distance between the light receiving element 34a and the light emitting element 34b.

The optical lens 34 may be disposed between the printed circuit board 36 and the detection sensor 32 and may be fixed to the printed circuit board 36 by the coupling with the detection sensor 32. The optical lens 34 may have a rectangular shape having a first side surface thereof having a concave shape and a second side surface thereof with a flat shape. Accordingly, the opposite side surfaces of the photo sensors 34, 34a, and 34b may be disposed to be toward the printed circuit board 36. The detection sensors 32 may be disposed at upper and lower portions, respectively, in a longitudinal direction of the optical lens 34 and the optical lens 34 may be fixed. The detection sensor 32 and the photo sensors 34, 34a, and 34b may have a concave shape to contact a part of an operator's body gripping the steering wheel 10. Therefore, a detection rate for the operator's body may be increased. For example, although a part of a body is expressed as thumbs among fingers of both hands, the present disclosure is not limited thereto. Therefore, fingers may approach the detection sensor 32, the detection may be made based on any finger other than the thumbs.

FIGS. 8A and 8B are exemplary diagrams illustrating another exemplary embodiment of the present disclosure. Describing another exemplary embodiment of the present disclosure with reference to FIGS. 8A and 8B, a vital signal detector 320 may be disposed outside the remote control switch 20. In other words, according to the exemplary embodiment of the present disclosure, the vital signal detector 320 may be disposed along with the buttons of the remote control switch 20, but according to another exemplary embodiment of the present disclosure as illustrated in FIG. 8A, the vital signal detector 320 may be formed to protrude from a horn switch 15 toward the rim.

In particular, referring to FIG. 8A, the vital signal detector 320 may include the photo sensor disposed between the plurality of detection sensors 322 and 324. The optical lens 340 of the photo sensor may have a width a of about 4 mm and a length b of about 16 mm in consideration of a width of a finger of the general public but is not limited thereto. Additionally, referring to FIG. 8B illustrating B-B of FIG. 8A, a distance c of a light receiving element 375 and a light emitting element 370 from a surface of the optical lens 340 may be limited to about 2 to about 2.5 mm and the light introduced from the exterior may be measured. For example, the width a, the length b, and the distance c of the optical lens 340 are not limited to the second exemplary embodiment and therefore the present exemplary embodiment may apply the above-mentioned values.

The operation of the detection apparatus of vital parameters on a steering wheel according to the exemplary embodiment of the present disclosure configured as described above will be described. FIG. 1 is an exemplary perspective view illustrating a detection apparatus of vital parameters on a steering wheel according to an exemplary embodiment of the present disclosure. FIG. 2 is an exemplary enlarged plan view of a part of FIG. 1. FIG. 7A is an exemplary plan view of the vital signal detector, and FIG. 7B is an exemplary bottom view of the vital signal detector. Describing the detection apparatus of vital parameters on a steering wheel according to the exemplary embodiment of the present disclosure with reference to FIGS. 1, 2, 7A, and 7B, the vital signal detector 30, the detection sensor 32 and the optical lens 34 may be fixed to the printed circuit board (PCB) having the light receiving element 34a and the light emitting element 34b disposed thereon. In particular, the distance between the light receiving element 34a and the optical lens 34 may be constantly maintained.

The printed circuit board 36 having the vital signal detector 30 mounted thereon may be mounted on the base 23 of the remote control switch 20. The printed circuit board 36 may be coupled with the base 23 while the base 23 being covered with the cover 26. In particular, a portion of the detection sensor 32 and the photo sensors 34, 34a, and 34b may be disposed to be exposed to the exterior through the plurality of button apertures formed on the cover 26. The detection may be more stably formed by the vital signal detector 30 exposed to the exterior environment of the remote control switch 20. Accordingly, a restriction on a material and a shape may be reduced and a freedom of design may be maintained.

Furthermore, the solder portions 32a' and 32b' of the detection sensor 32 may be fixed to the printed circuit board 36 and then soldered to increase the contact area due to the bead 40. Accordingly, the vital signal detector 30 may be more stably coupled with the remote control switch 20. When the vital signal detector 30 is coupled with the remote control switch 20 and the remote control switch 20 may be mounted on the steering wheel 10. The vital signal detector 30 may be positioned within the moving range of the driver's finger, and may thereby detect the vital parameters using fingers, (e.g., the thumb).

According to the detection apparatus of vital parameters on the steering wheel in accordance with the exemplary embodiment of the present disclosure, the vital signal detector may be integrally mounted in the remote control switch of the steering wheel. Further, according to the detection apparatus of vital parameters on the steering wheel, the separate space for the assembling portion of the vital signal detector is not required. Accordingly, the volume of the apparatus and the number of components may be reduced. The mountability and the aesthetic may be improved and operator's eyes may be maintained in a forward direction due to the concentration of the operator's eyes on the vital signal detector. Additionally, according to the detection apparatus of vital parameters on the steering wheel in accordance with the exemplary embodiment of the present disclosure, the vital signal detector may be more easily gripped when the driver grips the steering wheel. The vital signal detector may be embedded in the remote control switch to form the firm assembling configuration. The detection sensor may be fixed to the printed circuit board by the bolt and solder when the detection sensor is electrically connected to the printed circuit board. The detection apparatus of vital parameters on the steering wheel according to the exemplary embodiment may not restrictively apply the configuration and the method of the above-mentioned exemplary embodiments. That is, all or some of the respective exemplary embodiments may be selectively combined with each other so that they may be various modified.

The detection apparatus of vital parameters on a steering wheel according to the exemplary embodiments of the present disclosure may include the following effects.

First, the operator may grip the vital signal detector when gripping the steering wheel. The vital signal detector may be integrally mounted in the remote control switch of the steering wheel to remove the necessity of the separate assembling portion to improve the convenience of the driver.

Second, the vital signal detector may be embedded in the remote control switch to form the firm assembling configuration.

Third, when the detection sensor is electrically connected to the printed circuit board the detection sensor may be fixed to the printed circuit board due to the bolt and the solder.

However, the effects of the present disclosure are not limited to the above-mentioned effects and other effects which are not mentioned can be clearly understood to those skilled in the art from claims.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A detection apparatus of vital parameters on a steering wheel, comprising:
    a horn switch;
    a plurality of remote control switches configured to operate devices within a vehicle; and
    a vital signal detector configured to detect a vital signal of an operator, the vital signal detector mounted on a remote control switch of the plurality of remote control switches, wherein
    the vital signal detector includes a detection sensor configured to detect the vital signal of the operator, a photo sensor, and a printed circuit board coupled to the detection sensor and the photo sensor,
    the printed circuit board has bolting bores through which a bolt fixing the detection sensor and the photo sensor penetrates,
    the printed circuit board has apertures that abut the bolting bores,
    the detection sensor has a solder portion inserted into an aperture of the printed circuit board,
    the printed circuit board includes a bead that connects between the apertures,
    the bead is disposed to pass through at least one of the bolting bores, and
    the bead is formed with a bead aperture through which the bolt penetrates.

2. The detection apparatus according to claim 1, wherein the photo sensor further includes an optical lens and limits a contact area to a predetermined length and width to reduce a transmission of exterior light the optical lens.

3. The detection apparatus according to claim 2, wherein the detection sensor includes a plurality of conductors and the optical lens is disposed between the plurality of conductors.

4. The detection apparatus according to claim 3, wherein the optical lens is disposed between a printed circuit board and the detection sensor to be fixed to the printed circuit board by a coupling with the detection sensor.

5. The detection apparatus according to claim 2, wherein the photo sensor includes a light receiving element configured to absorb light and a light emitting element configured to emit light, and wherein the optical lens maintains a distance between the light receiving element and the light emitting element and is coupled with the printed circuit board.

6. The detection apparatus according to claim 1, wherein the vital signal detector includes a portion of the detection sensor and the photo sensor is exposed to the exterior of the remote control switch.

7. The detection apparatus according to claim 6, wherein the remote control switches are disposed in the horn switch adjacent to each other and each include the vital signal detector.

8. The detection apparatus according to claim 1, wherein the vital signal detector is disposed to abut to the steering wheel.

9. The detection apparatus according to claim 1, wherein the detection sensor and the photo sensor have a concave shape based on a predetermined curvature.

10. The detection apparatus according to claim 1, wherein the vital signal detector is configured to detect at least one of galvanic skin reflex, bioelectrical impedance analysis, photoplethysmography, and body mass index by a touch of the operator.

11. A detection apparatus of vital parameters on a steering wheel, comprising:
    a steering wheel;
    a remote control switch mounted on the steering wheel;
    a vital signal detector disposed on the remote control switch to abut the steering wheel, wherein the vital signal detector includes a detection sensor configured to detect a vital signal of an operator;
    a photo sensor disposed to cross the detection sensor; and
    a printed circuit board coupled to the detection sensor and the photo sensor, wherein
    the printed circuit board has bolting bores through which a bolt fixing the detection sensor and the photo sensor penetrates,
    the printed circuit board has apertures that abut the bolting bores,
    the detection sensor has a solder portion inserted into an aperture of the printed circuit board,
    the printed circuit board includes a bead that connects between the apertures,
    the bead is disposed to pass through at least one of the bolting bores, and
    the bead is formed with a bead aperture through which the bolt penetrates.

12. The detection apparatus according to claim 11, wherein the remote control switch includes:
    a base having a button portion of operating devices within a vehicle and that accommodates the vital signal detector; and
    a cover formed with a plurality of button apertures and coupled with the base to cover the base at an upper portion of the vital signal detector, wherein the detection sensor and the photo sensor are exposed to the exterior through any one of the plurality of button apertures.

* * * * *